United States Patent [19]
Wells

[11] Patent Number: 5,195,657
[45] Date of Patent: Mar. 23, 1993

[54] MANIFOLD LIQUID HANDLING DEVICE WITH BACKSIP FUNCTION

[75] Inventor: John R. Wells, Culver City, Calif.

[73] Assignee: Source Scientific Systems, Garden Grove, Calif.

[21] Appl. No.: 517,562

[22] Filed: Apr. 30, 1990

[51] Int. Cl.[5] .................................................. B01L 3/02
[52] U.S. Cl. .......................................... 222/1; 222/204; 222/330; 222/571; 422/100; 73/864.11
[58] Field of Search .............. 222/571, 204, 108, 109, 222/416, 1, 152, 330; 422/99, 100; 73/864.11

[56] References Cited

U.S. PATENT DOCUMENTS

| | | | |
|---|---|---|---|
| 2,728,491 | 12/1955 | Aneshansley | 222/211 X |
| 2,761,590 | 9/1956 | Du Bois | 222/211 |
| 2,763,404 | 9/1956 | Pollnow | 222/511 X |
| 2,779,506 | 1/1957 | Gajda | 222/571 |
| 2,783,919 | 3/1957 | Ansell | 222/211 |
| 3,157,319 | 11/1964 | Schwienbacher | 222/207 |
| 4,149,315 | 4/1979 | Page, Jr. et al. | 222/571 X |
| 4,324,349 | 4/1982 | Kaufman | 222/211 X |
| 4,635,665 | 1/1987 | Namba et al. | 15/302 X |

Primary Examiner—Kevin P. Shaver
Attorney, Agent, or Firm—Susan L. Preston

[57] ABSTRACT

Leakage from the manifold of a manifold type multichannel dispenser, aspirator, or washer may be diminished by employing siphon shaped pipettes and backsipping liquid from the long leg of such siphon shaped pipettes after each use of the device. The siphon shaped pipettes may be attached to the top-most part of the manifold so as to facilitate the purging of bubbles therefrom.

8 Claims, 1 Drawing Sheet 005,195,657

MANIFOLD LIQUID HANDLING DEVICE WITH BACKSIP FUNCTION

BACKGROUND

The invention relates to liquid handling devices. More particularly, the invention relates to devices and methods for simultaneously transferring liquid to or from multiple vessels.

A number of laboratory applications require that identical aliquots of liquid be transferred to or from multiple vessels. For example, some immunoassays employ a wash step in which identical aliquots of wash liquid are dispensed into an array of test tubes. This dispensing step may then be followed by an aspiration step in which the wash liquid is removed from each test tube. If the array of test tubes is large, this wash protocol becomes tedious if it is performed serially, i.e. one test tube at a time. As a consequence, multi-channel liquid handling devices have been developed which substantially shorten the time required to perform such protocols.

A multi-channel liquid handling device is a device which can simultaneously dispense and/or simultaneously aspirate liquid with respect to an array of vessels, i.e. two or more vessels having a fixed geometric relationship with respect to one another. The multi-channel liquid handling device includes an array of liquid conductors for simultaneously conducting liquid to or from each vessel within the array of vessels. The geometry of the array of liquid conductors corresponds to the geometry of the array of vessels so that each liquid conductor can interact with a corresponding vessel in conjunction with similar simultaneous interactions by the remaining liquid conductors and vessels.

Each liquid conductor within a multi-channel liquid handling device is connected to a source of liquid and/or vacuum. A liquid source is employed for dispensing liquid; a vacuum source is employed for aspirating liquid. A multi-channel liquid handling device may be constructed with multiple sources or with a single source. If the multi-channel liquid handling device employs multiple sources, each individual liquid conductor may be coupled to its own source. On the other hand, if the multi-channel liquid handling device employs a single source, a manifold may be employed to mediate the coupling between the array of liquid conductors and the source.

A manifold type multi-channel device is disclosed by Namba et al. (U.S. Pat. No. 4,635,665). Namba's device includes both a dispensing function and an aspiration function for transferring liquid to and from an array of wells. The dispensing function employs a manifold connected to a liquid source. The aspiration function employs a manifold connected to a vacuum source. Attached to each manifold is an array of pipettes for conducting liquid to or from the manifold. The pipettes descend from their respective manifolds. Charging the dispensing manifold with liquid allows liquid to be expressed from the array of descending pipettes. Charging the aspiration manifold with a vacuum and submerging the tips of the pipettes into liquid allows liquid to be aspirated from the array of microtiter plate wells.

It disclosed herein that, under certain circumstances, when manifold type multi-channel devices are deactivated, they may be subject to a type of leakage which is caused by siphoning. What was needed was an anti-siphon feature to prevent leakage from manifold type multi-channel dispensing and/or aspiration devices.

SUMMARY

The Problem

The invention discloses that there can be a leakage problem with respect to manifold type dispensers and aspirators. The leakage mechanisms for dispensing and aspiration manifolds differ somewhat from one another.

A dispensing manifold which is fully charged with liquid but otherwise unactivated, i.e. unpressurized, may leak by means of a siphon mechanism. Connected to the manifold is an array of descending pipettes. The pipettes are of equal length and their tips are aligned with one another. Normally, the manifold is held in a horizontal position with the tips of the pipettes forming a horizontal line. However, if the manifold is cocked or tilted so as to displace the tips of the pipettes from their horizontal line, liquid may drain from the manifold by means of a siphon mechanism. Liquid will leak from the lowest tip and air will enter into the highest tip. Even if the manifold and tips are maintained in their horizontal configuration, leakage may be initiated if an inertial jolt drives liquid from one pipette and causes air to be drawn into another. Such an inertial jolt may occur if the dispensing manifold is translated from one array of vessels to another by means of a sudden acceleration or deceleration.

The mechanism of leakage from an aspiration manifold may differ from the mechanism of leakage from a dispensing manifold. After a manifold liquid aspirator has completed its function, the apparatus may be turned off, i.e. the vacuum source may be deactivated. However, prior to deactivating the vacuum source, liquid may be purged from the aspiration manifold by continuing to draw air through the pipettes for a period. If the purge is incomplete for any reason, residual liquid may remain. Such residual liquid may find its way back into one or more of the pipettes. Residual liquid in a pipette connected to a manifold may behave differently from residual liquid in a closed pipette. In a closed pipette, residual liquid will descend within the pipette until a pressure differential is formed within the pipette which is sufficient to support the weight of the liquid. On the other hand, residual liquid in a pipette connected to a manifold can can descend within the pipette without forming a pressure differential. In a aspiration manifold, the descent of residual liquid within one pipette will cause air to be drawn into the manifold through the remaining unclogged pipettes. No pressure differential will form within pipettes. The aspiration manifold need not be cocked, tilted, or jarred for this particular leakage mechanism to occur.

The Solution

The invention teaches that the same solution may be employed to diminish siphon type leakage both from manifold type dispensers and manifold type aspirators. The manifold type multi-channel washing device of the invention employs siphon shaped pipettes connected to the dispensing and/or apspirating manifold. Each siphon shaped pipette includes a short leg and a long leg. In the preferred embodiment, the short legs of the pipettes are connected to the top-most part of the manifold and ascend therefrom. The short legs are joined to the long legs at a junction having an elevation which exceeds the elevation of the top-most part of the manifold. The long legs then descend from that junction to an elevation below the manifold and terminate with an opening for the release of liquid.

Normally, it might be thought that use of such siphon shaped pipettes would merely exacerbate any leakage arising from a siphon mechanism. However, the invention further includes a backsip function. The invention teaches that after each dispensing or aspiration function, all liquid must be withdrawn from the long leg of the siphon shaped pipettes. Withdrawal of liquid from each of the long legs effectively eliminates the possibility of leakage by means of a siphon mechanism. This solution to the leakage problem is unavailable to manifold devices which employ conventional pipettes, i.e. straight pipettes not having a siphon configuration.

The use of siphon shaped pipettes also benefits the dispensing function with respect to the process of charging the manifold with liquid. If the siphon shaped pipettes are attached to the top-most part of the dispensing manifold, air and bubbles will be purged from the manifold as the manifold is charged with liquid. The elimination of bubbles from the manifold renders the device more responsive to liquid flow.

DETAILED DESCRIPTION

The Device

A preferred embodiment of a manifold type multi-channel liquid dispenser is illustrated in FIG.'S 1-3. A cylindrically shaped manifold (1) is connected to a liquid source (2). The liquid source (2) may be conventional with a liquid reservoir and a pump. Activating the pump or liquid source (2) causes liquid (3) to be driven or expressed from the reservoir to the manifold (1). Deactivating the pump or liquid source (2) terminates the flow of liquid (3) from the reservoir to the manifold (1). The manifold (1) is charged by activating the pump and driving sufficient liquid (3) into the manifold (1) so as to fill the manifold (1).

Figure 1:
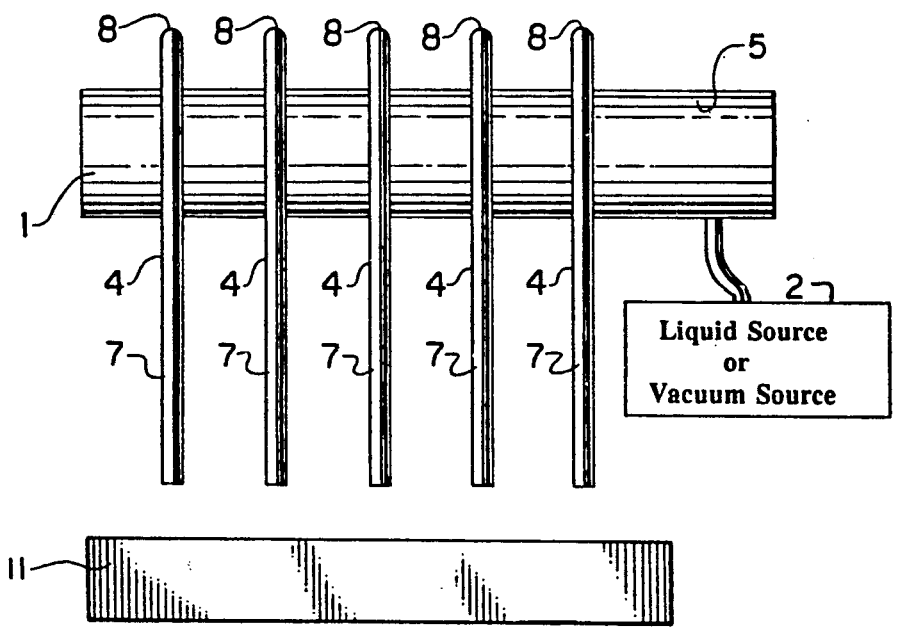
FIG. 1 is a plan view of the front of a microtiter plate and of a manifold type multi-channel dispensing device illustrating a dispensing manifold and five siphon shaped pipettes ascending therefrom.
Figure 2:
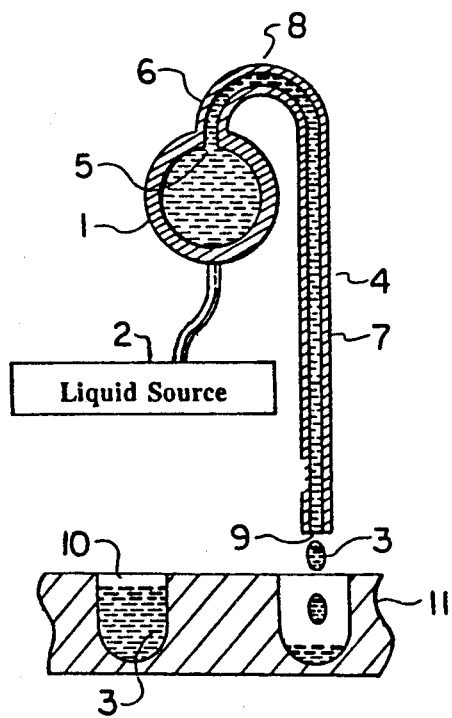
FIG. 2 is a sectional view of the device and microtiter plate of FIG. 1 illustrating the dispensing of liquid into a microtiter well.
Figure 3:
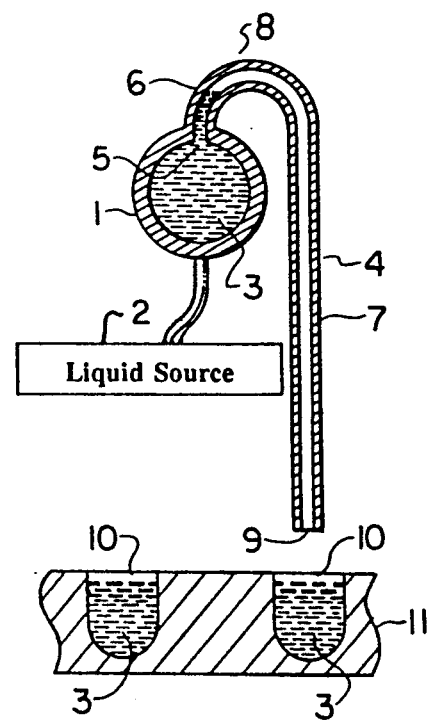
FIG. 3 is identical to FIG. 2 except that it illustrates the withdrawal of liquid from the long leg of the siphon shaped pipette.

Connected to the manifold (1) is an array of siphon shaped pipettes (4). FIG. 1 illustrates an array of five pipettes (4). In a preferred embodiment, the pipettes (4) are connected to the top-most part (5) of the manifold (1). If the manifold (1) is cylindrical in shape as illustrated in FIG.'S 1 and 2, the top-most part (5) of the manifold may consist of an area or line extending the length of the manifold. Connecting the pipettes (4) to the top-most part (5) of the manifold facilitates the charging of the manifold (1) by allowing air and bubbles to escape from the manifold (1) through the pipettes (4). After the manifold (1) is charged with liquid (3), further activation of the liquid source (2) causes liquid (3) to flow through the pipettes (4).

Each of the pipettes (4) has the configuration of a siphon with short leg (6) and a long leg (7). The short leg (6) is connected to the manifold (1) and ascends therefrom. The short leg (6) and long leg (7) meet and join at a bend (8). The long leg (7) descends from the bend (8) and terminates with tip opening (9) having an elevation below the manifold from which liquid (3) is dispensed. When the device is oriented in its proper operating position, the bend (8) has an elevation which exceeds the elevation of both the top-most part (5) of the manifold (1) and of the tip or opening (9) of the long leg (7).

The preferred embodiment of the manifold type multi-channel dispenser also includes a backsip function, i.e. a means for withdrawing liquid (3) from the long legs (7) of the pipettes (4) after each dispensing function. The backsip function draws the liquid (3) in a direction which is opposite direction by which the liquid (3) is expressed, i.e. the liquid (3) is withdrawn from the pipettes (4) toward the manifold (1).

A preferred embodiment for a manifold type multi-channel liquid aspirator may be constructed identically to the structure of the above described manifold type multi-channel liquid dispenser except that a vacuum source is substituted for the liquid source (2).

A manifold type multi-channel washer may be constructed by combining the above described manifold type multi-channel liquid dispenser and manifold type multi-channel liquid aspirator. In the preferred manifold type multi-channel washer, the dispenser and aspirator are joined to one another with an orientation such that each pipette tip (9) for the dispenser is juxtaposed to a corresponding pipette tip for the aspirator. This juxtaposition results in the formation of an array of paired pipette tips, with one dispensing tip (9) and one aspiration tip within each pair. The configuration of this array of paired tips is designed to correspond to the configuration of the array of vessels, e.g. microtiter wells (10) or racked test tubes.

The Method

The manifold type multi-channel dispenser described above may be employed in conjunction with an improved dispensing method so as to dispense liquid (3) without leakage due to siphon mechanisms. In the first step of the improved disensing method, the manifold (1) is charged with liquid (3) by driving liquid (3) from the liquid source (2). Driving liquid into the manifold displaces the air therein. The displaced air is pushed to the top-most part (5) of the manifold (1), where it escapes through the pipettes (4) attached thereto. Once the manifold (1) is charged with liquid (3), further displacement of liquid into the manifold (1) causes liquid (3) to be expressed or dispensed from the manifold (1) through the attached pipettes (4). The expression of liquid from the manifold (1) may be terminated by deactivating the liquid source (2), i.e. switching off the pump. In order to prevent siphon type leakage from the manifold (1) after the above expression step, a backsip function may be employed. After expressing liquid (3) from the manifold (1), liquid (3) within the long leg (7) portion of the pipettes (4) is withdrawn, i.e. backsipped, back into the manifold (1). Backsipping the liquid from the long legs (7) prevents siphon type leakage from the manifold (1).

With respect to aspiration procedures, the manifold type multi-channel aspirator described above may be employed in conjunction with an improved aspirating method so as to aspirate liquid (3) without leakage due to siphon mechanisms. This improved method for aspirating liquid (3) effectively eliminates leakage from the manifold (1) caused by siphon mechanisms. In the first step of the improved aspirating method, a vacuum is drawn from the manifold (1) by activating the vacuum source The tips of the pipettes (4) are then immersed in the liquid (3) held by an array of vessels, e.g. microtiter wells (10), and the liquid (3) is aspirated therefrom. During the aspiration step, liquid (3) rises through the pipettes (4) and passes through the manifold (1) and into the vacuum source. The aspiration process may be terminated by exhausting the liquid (3) from the array of vessels or by removing the tips of the pipettes (4) from the vessels. After the aspiration step is terminated, air continues to be drawn through the manifold (1) so as to withdraw liquid (3) from the long leg (7) of the siphon shaped pipettes (4) and so as to eliminate as much liquid (3) as possible from the manifold (1). When the vacuum source is deactivated, the siphon configuration of the pipettes (4) effectively prevents siphon type leakage of residual liquid (3) within the manifold (1).

With respect to washing procedures, the manifold type multi-channel washer described above may be employed in conjunction with an improved washing method so as to wash vessel arrays (11) without leakage due to siphon mechanisms. This improved method for washing microtiter plates (11) effectively eliminates leakage from the manifolds (1) caused by siphon mechanisms. In essence, the improved washing method combines the above described methods for dispensing and aspirating liquids. The aspiration steps result in the removal of liquids (3) from an array of vessels (10). The dispensing steps result in the expression of wash liquid (3) into the same array of vessels (10). The end product of this washing method is an array of uniformly washed vessels (10), without leakage of wash liquid or aspirated liquids.

What is claimed is:

1. An improved manifold type multi-channel liquid dispenser of the type having:
    a liquid source which is activatable for expressing liquid,
    a manifold connected to said liquid source, said manifold having a top-most part, and
    a plurality of pipettes connected to said manifold for guiding liquid therefrom when liquid is expressed from said liquid source,
    wherein the improvement comprises:
        each of said pipettes having the configuration of a siphon with a short leg and a long leg, the short leg being connected to said manifold and ascending therefrom, the short leg forming a bend at an elevation exceeding the top-most part of said manifold, the long leg joining the short leg at the bend and descending therefrom, the long leg terminating with an opening at an elevation below the top most part of said manifold, and
        said liquid source including a means for withdrawing liquid from the long leg of each of said pipettes,
    whereby after expressing liquid from said pipettes, leakage from said pipettes may be prevented by withdrawing liquid from the long leg of each of said pipettes.

2. An improved manifold type multi-channel liquid dispenser as described in claim 1 wherein the improvement further comprises:
    each of said pipettes being connected to and opening onto said manifold at an elevation substantially equivalent to the top-most part of said manifold.

3. An improved manifold type multi-channel liquid aspirator of the type having:
    a vacuum source which is activatable for aspirating liquid,
    a manifold connected to said vacuum source, and
    a plurality of pipettes connected to said manifold for guiding liquid thereto when said vacuum source is activated,
    wherein the improvement comprises:
        each of said pipettes having the configuration of a siphon with a short leg and a long leg, the short leg being connected to said manifold and ascending therefrom, the short leg forming a bend, the long leg joining the short leg at the bend and descending therefrom, the long leg terminating with an opening,
    whereby after aspirating liquid through said pipettes, leakage from said pipettes may be prevented by withdrawing liquid from the long leg of each of said pipettes.

4. An improved manifold type multi-channel washer having a combined manifold type multi-channel liquid dispenser and liquid aspirator, the manifold type multi-channel liquid dispenser being of the type having:
    a liquid source which is activatable for expressing liquid,
    a dispensing manifold connected to said liquid source, said dispensing manifold having a top-most part, and
    a first plurality of pipettes connected to said dispensing manifold for guiding liquid therefrom when liquid is expressed from said liquid source,
    the manifold type multichannel aspirator being of the type having:
    a vacuum source which is activatable for aspirating liquid,
    an aspiration manifold connected to said vacuum source, and
    a second plurality of pipettes connected to said aspiration manifold for guiding liquid thereto when said vacuum source is activated,
    wherein the improvement comprises:
        each of said first and second plurality of pipettes having the configuration of a siphon with a short leg and a long leg, the short leg being connected to said manifold and ascending therefrom, the short leg forming a bend, the long leg joining the short leg at the bend and descending therefrom, the long leg terminating with an opening,
        each of the bends of said first plurality of pipettes having an elevation exceeding the elevation of the top-most part of said dispensing manifold,
        said liquid source including a means for withdrawing liquid from said dispensing manifold and from the long leg of each of said first plurality of pipettes,
    whereby, after expressing liquid from said first plurality of pipettes, leakage from said first plurality of pipettes may be prevented by withdrawing liquid from the long leg of each of said first plurality of pipettes and
    whereby, after aspirating liquid through said second plurality of pipettes, leakage from said second plurality of pipettes may be prevented by withdrawing liquid from the long leg of each of said second plurality of pipettes.

5. An improved manifold type multi-channel liquid dispenser as described in claim 4 wherein the improvement further comprises:
    each of said first plurality of pipettes being connected to and opening onto said dispensing manifold at an elevation substantially equivalent to the top-most part.

6. An improved method for dispensing liquid into an array of liquid vessels, the method being of the type having the following steps:
Step A: charging a manifold with a liquid from a liquid source; then
Step B: expressing liquid simultaneously from the manifold through a plurality of pipettes; and then
Step C: terminating the expression of liquid;
wherein the improvement comprises:
in said Step B, the liquid being expressed through pipettes having a configuration of a siphon with both a long leg and a short leg; the
after said Step C,
Step D: withdrawing liquid from the long leg of each of the pipettes for preventing leakage from the manifold.

7. An improved method for aspirating liquid from an array of liquid vessels, the method being of the type having the following steps:
Step A: drawing a vacuum from a manifold from a vacuum source; then
Step B: aspirating liquid simultaneously into the manifold through a plurality of pipettes; and then
Step C: terminating the aspiration of liquid;
wherein the improvement comprises:
in said Step B, the liquid being aspirated through pipettes having a configuration of a siphon with both a long leg and a short leg; then
after said Step C,
Step D: withdrawing liquid from the long leg of each of the pipettes for preventing leakage from the manifold.

8. An improved method for washing an array of liquid vessels including a combination of liquid dispensing and liquid aspiration methods, the liquid dispensing method being of the type having the following steps:
Step A: charging a dispensing manifold with liquid; then
Step B: expressing liquid simultaneously from the dispensing manifold through a first plurality of pipettes; and then
Step C: terminating the expression of liquid;
the liquid aspiration method being of the type having the following steps:
Step D: drawing a vacuum from an aspiration manifold; then
Step E: aspirating liquid simultaneously int the aspiration manifold through a second plurality of pipettes; and then
Step F: terminating the aspiration of liquid;
wherein the improvement comprises:
in said Step B, the liquid being expressed through first pipettes having a configuration of a siphon with both a long leg and a short leg; then
after said Step C,
Step C(1): withdrawing liquid from the long leg of each of the first pipettes for preventing leakage from the dispensing manifold,
in said Step E, the liquid being aspirated through the second pipettes having a configuration of a siphon with both a long leg and a short leg; then
after said Step F,
Step F(1): withdrawing liquid from the long leg of each of the second pipettes for preventing leakage from the aspiration manifold.

* * * * *